United States Patent [19]

Mirviss et al.

[11] Patent Number: 5,760,199
[45] Date of Patent: Jun. 2, 1998

[54] POLYSACCHARIDE ACID AMIDE COMPRISING FATTY ALKYL GROUP IN AMIDE

[75] Inventors: Stanley B. Mirviss, Stamford, Conn.; Meiylin F. Antezzo, Carmel, N.Y.

[73] Assignee: Akzo Nobel nv, Arnhem, Netherlands

[21] Appl. No.: 502,202

[22] Filed: Jul. 13, 1995

[51] Int. Cl.$^6$ .................................. C07H 5/00
[52] U.S. Cl. ............. 536/18.7; 536/55.1; 536/123.1; 536/123.13
[58] Field of Search ............ 536/18.7, 55.1, 536/123.1, 123.13

[56] References Cited

U.S. PATENT DOCUMENTS

| | | | |
|---|---|---|---|
| 2,662,073 | 12/1953 | Mehltretter et al. | 260/102 |
| 2,752,334 | 6/1956 | Walton | 260/211 |
| 3,679,659 | 7/1972 | Zak | 260/209 R |
| 5,064,659 | 11/1991 | Greenberg et al. | 426/3 |
| 5,296,588 | 3/1994 | Au et al. | 536/1.11 |
| 5,336,765 | 8/1994 | Au et al. | 536/18.5 |

FOREIGN PATENT DOCUMENTS

| | | | |
|---|---|---|---|
| 550 278 | 7/1993 | European Pat. Off. | C11D 1/66 |
| 550 281 | 7/1993 | European Pat. Off. | A61K 7/50 |
| 550106 | 7/1993 | European Pat. Off. | C07H 15/04 |
| WO 92/08675 | 5/1992 | WIPO | C02F 1/58 |

OTHER PUBLICATIONS

J.C.P. Albarran et al., "Limitations of the Aminonitrile Synthesis: New Products from D–Glucose, D–Galactose, and D–Mannose", Carbohydrate Research, 143 (1985) 117–128.

P. Scholnick et al., "Technical Notes: Iron Chelating Capacity of Gluconamides and Lactobionamides", J. Dairy Sci. 1980, 63: 471–473.

Derwent Patent Abstract 89–232294/32 (1989).

Derwent Patent Abstract 08571V/05 (1974).

Derwent Patent Abstract 07680V/05 (1974).

H. Parekh et al., "Studies on Aminosugars. I. Synthesis of Optically Active N–Aryl–D–Glucoheptosaminonitriles", J. Indian Chem. Soc., vol. 49, No. 11, 1972, 1147–1150.

*Primary Examiner*—Elli Peselev
*Attorney, Agent, or Firm*—Richard P. Fennelly; Louis A. Morris

[57] ABSTRACT

Polysaccharide acid amide compositions are disclosed which contains one extra carbon atom as compared to the polysaccharide and which comprises an acid amide of the formula —C(O)N(R)(R') where R is selected from the group consisting of hydrogen and alkyl of from about one to about four carbon atoms and R' is fatty alkyl of no less than about eight carbon atoms. Disaccharides such as lactose or maltose are preferred. These polysaccharide acid amides are formed by reacting the polysaccharide with a cyanide source, for example, an alkali metal cyanide, such as sodium cyanide, in the presence of an amine reagent containing a fatty alkyl group, such as one which comprises a ammonium ion of the formula $H_2N(R)(R')$ where R is selected from the group consisting of hydrogen and alkyl of from about one to about four carbon atoms and R' is fatty alkyl of no less than about eight carbon atoms.

14 Claims, No Drawings

POLYSACCHARIDE ACID AMIDE COMPRISING FATTY ALKYL GROUP IN AMIDE

BACKGROUND OF THE INVENTION

A wide variety of chemical compounds possessing surfactant properties are known to persons of ordinary skill in the art including those which possess hydroxyalkylene moieties and/or fatty alkyl amine moieties. Some representative prior art references which illustrate such compounds include:

1. U.S. Pat. Nos. 5,174,927 and 5,188,769 which cover polyhydroxy fatty acid amides of the general formula

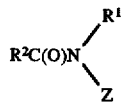

where $R^1$ can be hydrogen or certain lower alkyl group-containing substituents, $R^2$ can be fatty alkyl and Z is a polyhydroxyhydrocarbyl group;

2. U.S. Pat. No. 5,004,564 which discloses certain glycaminoacetic acid/acetates of the formula

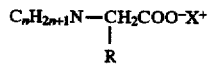

where, n can range from 4 to 24, thus including fatty alkyl, R can be a hydroxyalkylene-containing substituent, and X is sodium, potassium, or hydrogen; and 3. French Patent No. 2,523,962 which describes certain N-fatty alkyl amidosugars of the general formula

where m can range from 2 to 6 and R is a $C_6$–$C_{18}$ alkyl group, such as fatty alkyl. The compounds shown in this French patent are said to be prepared by reaction of aldonic acid (which actually will not work) or the corresponding lactone (which will work) with the desired amine. Glucono-lactone is the preferred reagent. Such a preparatory procedure requires the use of a relatively expensive starting material and is relatively more complex than desired;

4. U.S. Pat. No. 2,662,073 describes gluconamides which are prepared by condensing long chain aliphatic or cycloaliphatic primary amines with δ-gluconolactone;

5. U.S. Pat. No. 5,084,270 describes N-alkoxyalkylamides which are formed by reacting a specific type of amine compound with a carboxylic acid or lactone having a particular structure. It has been found that only the lactone reagent described for use in this patent will give an amidosugar. Use of the acid will not; and 6. U.S. Pat. Nos. 5,296,588 and 5,336,765 describe the use of aldonolactone and aldobiono-1,5-lactone to prepare N-substituted aldonamides and aldobionamides, respectively.

Previously reported reactions between glucose, amines, and hydrogen cyanide or potassium cyanide are reported to give the α-aminonitrile derivatives of the sugar. (See H. Parekh et al., J. Indian Chem. Soc., Vol. 49, No. 11, 1972, pp. 1147–1150 and R. Kuhn et al., Justus Liebigs Ann. Chem., 1956, Vol. 600, pp. 115–124).

Copending U.S. application Ser. No. 08/159,390, which has been refiled in the form of continuation-in-part, as U.S. application Ser. No. 08/576,893 on Dec. 22, 1995 of A. A. Fleming et al. describes a process for the formation of an N-fatty alkyl amidosugar which comprises the reaction of an aldose, ketose, or mixture thereof with cyanide and fatty amine to form the N-fatty alkyl amidosugar of the formula

where m can range from about 3 to about 14, R is fatty alkyl, and R' is either hydrogen or alkyl.

SUMMARY OF THE INVENTION

The present invention, in one embodiment, relates to novel polysaccharide acid amide compositions which contain one extra carbon atom as compared to the polysaccharide and which comprise a fatty alkyl group in the amide, which is preferably of the formula —C(O)N(R) (R'), where R is selected from the group consisting of hydrogen and alkyl of from about one to about four carbon atoms and R' is fatty alkyl of no less than about eight carbon atoms. Disaccharide acid amides, such as those of either lactose or maltose are exemplary.

The present invention, in another embodiment, relates to a novel process of forming the aforementioned polysaccharide acid amide compositions by reacting the polysaccharide with a cyanide source, for example, an alkali metal cyanide, as exemplified by sodium cyanide, in the presence of an amine reagent containing a fatty alkyl group, such as by using an ammonium moiety of the formula $H_2N(R)$ (R'), where R and R' are as defined above.

DESCRIPTION OF PREFERRED EMBODIMENTS

In the process described above, a variety of solvents can be selected for use, including water, alcohol, or mixtures of water and alcohol. Because of the moderate to poor solubility of the disaccharide starting material in alcohol, it is preferred, but not necessary, to include some water if an alcohol solvent is the solvent of choice. The presence of such water helps to increase the cyanide salt solubility as well.

Preferred for use as reagents herein are the so-called "reducing" disaccharides which are materials which reduce Fehling's solution (see, for example, Organic Chemistry, 3rd edition, Fieser and Fieser, Reinhold, 1956, page 350). Examples of such reagents include lactose, maltose, cellobiose, and the like.

The amine reagent which is to be used is a fatty amine containing from about six to about twenty-two carbon atoms in the alkyl groups contained therein, preferably those containing straight chain alkyl groups. It is also possible to utilize amines containing branched chain alkyl groups, such as the 2-ethylhexyl group. Most preferred are the primary amines since the secondary amines react more sluggishly.

The cyanide salt reagent is preferably an alkali metal cyanide, such as sodium or potassium cyanide, but other cyanides can be used, such as calcium or magnesium cyanide. The silyl cyanides can be selected for use, if desired.

Generally a 1:1:1 molar ratio of cyanide:polysaccharide::amine is used in practicing the process of the present invention, but a slight deficiency of cyanide helps to insure a cyanide-free product. Thus, a ratio of 0.90 to 0.95:1:1, as defined above, is preferably employed. The amine is advantageously used as the hydrohalide or hydrogen sulfate salt. This salt may be generated in situ during the reaction, if desired. The amine salt is usually added to the reaction medium along with the polysaccharide and solvent. An equally suitable alternative is to add the amine and solvent followed by a mineral acid, such as hydrochloric acid, hydrobromic acid, sulfuric acid, or phosphoric acid, to form the ammonium salt of the desired amine. The polysaccharide is then added. The cyanide is best, but not necessarily, added last and is best added slowly, preferably as a solution. The addition of the cyanide reactant last will minimize the amount of carboxylic acid by-product formed. This by-product corresponds to the sugar acid part (or moiety) of the sugar amide product.

The temperature at which the above-described reagents can be reacted ranges from below room temperature all the way up to the reflux temperature of the chosen solvent. A suitable temperature range is from about 15° C. to about 85° C. The reaction is slower at lower temperatures and produces a darker colored product at higher temperatures. A preferred temperature range is from about 40° C. to about 75° C.

The time needed to essentially complete the reaction will vary depending upon the reaction temperature, the degree of mixing during the reaction (good stirring is important to optimize product yield), and the concentration of reactants. A suitable time range is from one to twenty-four hours. The progress of the reaction can be followed by using well known analytical techniques to measure the disappearance of one or more of the reactants.

The product is generally a solid which can be filtered off from the total reaction product which is obtained. More of the desired product can be recovered by distillation or evaporation of the filtrate. Product solubility will depend upon the water content of the solvent and the chain length of the alcohol, if an alcohol is used as, or in, the solvent component. The presence of higher amounts of water will render the product increasingly more soluble.

Traces of cyanide may be present in the product, depending, in part, on the molar ratio of the reactants that are employed. Much of this can be removed by water washing in the cold to minimize product loss in the water. The presence of hydrogen peroxide or bleach in the wash water enhances cyanide removal. Treatment of the product with alkaline (pH of 10–12) aqueous formaldehyde solution is an alternative cyanide removal technique. Ferrous or ferric ions will also remove cyanide ion but they contaminate the product. Both hydrogen peroxide and alkaline formaldehyde work well to reduce cyanide contamination to below 1–2 ppm. Sulfur duioxide or bisulfite may also be utilized but they may lead to contamination of the product.

Traces of amine may be present in the product as well. These may be removed by washing the product with an alcohol (or other organic) solvent. It is possible to remove both cyanide and unreacted amine simultaneously by washing with alcoholic formaldehyde or alcoholic hydrogen peroxide.

The present invention is illustrated by the Examples which follow.

EXAMPLE 1

A three neck 250 ml flask was charged with 17.1 gm of lactose (0.05 mole) and 11.0 gm dodecylamine hydrochloride (ARMEEN 12D-HCl) with 75 ml of water. The solution was stirred at 60° C. for two hours. Then, 2.45 gm of sodium cyanide (0.05 mole) was added and the mixture was stirred at 60° C. overnight. The water was removed by vacuum (freeze drying). The product, by nmr analysis gave an approximate 10–20% yield of the homologous $C_{13}$ sugar acid amide of the dodecylamine and approximately 10–20% yield of the homologous $C_{13}$ sugar acid.

EXAMPLE 2

This Example was carried out in the same manner as Example 1 with use, as a reaction solvent, of a mixture of 52 ml of ethanol and 23 ml of water. The formation of the above-described sugar amide and sugar acid were found by nmr analysis of the product in about the same yield as reported in Example 1.

EXAMPLE 3

A reaction flask was charged with 0.55 gm of lactose (0.025 mole), 7.65 gm of octadecylamine hydrochloride (0.025 mole), 20 ml of water, and 46 ml of methanol. The mixture was stirred at 60° C. for one hour. Then, 1.22 gm of sodium cyanide (0.025 mole) was added, and the resulting reaction mixture was stirred at 60° C. for about twenty-four hours. A solid formed upon cooling which was filtered off and then air dried for two days. The product weighed 10.39 gm (65% yield) which analyzed $^{13}C$ CPMAS nmr to be essentially all $C_{13}$ carbon sugar acid amide homologous to the twelve carbon sugar acid, lactobionic acid. The filtrate contained little of the sugar amide but did contain some of the thirteen carbon atom sugar acid.

EXAMPLE 4

The procedure performed pursuant to this Example was similar to that performed in Example 3 with the exception that a tallow-derived amine containing 43% oleyl, 20% stearyl, 24% palmityl, and the rest a mixture of $C_{14}$ to $C_{18}$ saturated and unsaturated amines (ARMEEN TD brand) was used. A solid was isolated and dried and weighed 11.03 gm for a 62% yield.

EXAMPLE 5

A large scale run was made similar to the one described in Example 3 using 131.8 gm (0.35 mole) of lactose, 82.8 gm (0.385 gm) of cocoamine (ARMEEN CD brand containing 50% lauryl, 18% myristyl, 8.5% palmityl, 7% octyl, 6% oleyl, 6% decyl, 3% stearyl with traces of other amines), and 17.15 gm of sodium cyanide. The solvents used were 300 ml of methanol and 150 ml of water. The solids formed upon cooling the reaction mixture were filtered and dried. The solid product weighed 90 gm The filtrate was evaporated to dryness with vacuum, and the solid had a weight of 84 gm. The total weight of desired product was 174 gm which was a yield of 87%.

The foregoing Examples, since they illustrate only certain embodiments of the present invention, should not be construed in a limiting sense. The scope of protection sough is set forth in the claims which follow.

We claim:

1. A compound selected from the group consisting of a disaccharide acid amide compound and a polysaccharide acid amide compound which contains one extra carbon atom as compared to the disaccharide or polysaccharide and which comprises a fatty alkyl group in the amide.

2. A compound as claimed in claim 1 wherein the disaccharide is lactose.

3. A compound as claimed in claim 1 wherein the disaccharide is maltose.

4. A compound selected from the group consisting of a disaccharide acid amide compound and a polysaccharide acid amide compound which contains one extra carbon atom as compared to the disaccharide or polysaccharide and which comprises an acid amide of the formula —C(O)N(R) (R'), where R is selected from the group consisting of hydrogen and alkyl of from about one to about four carbon atoms and R' is fatty alkyl of no less than about eight carbon atoms.

5. A compound as claimed in claim 4 wherein the disaccharide is lactose.

6. A compound as claimed in claim 4 wherein the disaccharide is maltose.

7. A process for forming a compound selected from the group consisting of a disaccharide acid amide compound and a polysaccharide acid amide compound which contains one extra carbon atom as compared to the disaccharide or polysaccharide and which comprises a fatty alkyl group in the amide which comprises reacting the disaccharide or polysaccharide with a cyanide source in the presence of an amine reagent containing a fatty alkyl group.

8. A process as claimed in claim 7 wherein the disaccharide is lactose.

9. A process as claimed in claim 7 wherein the disaccharide is maltose.

10. A process as claimed in claim 7 wherein the amine reagent comprises a ammonium ion of the formula $H_2N(R)(R')$ where R is selected from the group consisting of hydrogen and alkyl of from about one to about four carbon atoms and R' is fatty alkyl of no less than about eight carbon atoms.

11. A process as claimed in claim 7 wherein the cyanide source is an alkali metal cyanide.

12. A process as claimed in claim 7 wherein the cyanide source is sodium cyanide.

13. A process as claimed in claim 10 wherein the cyanide source is an alkali metal cyanide.

14. A process as claimed in claim 10 wherein the cyanide source is sodium cyanide.

* * * * *